United States Patent [19]

Hurtel

[11] Patent Number: 4,859,793
[45] Date of Patent: Aug. 22, 1989

[54] PROCESS FOR THE PRODUCTION OF FLUOROALKYL ACRYLATES

[75] Inventor: Patrice Hurtel, Saint Avold, France

[73] Assignee: Societe Chimique des Charbonnages S.A., Paris, France

[21] Appl. No.: 132,431

[22] Filed: Dec. 11, 1987

Related U.S. Application Data

[63] Continuation-in-part of Ser. No. 875,826, Jun. 18, 1986.

[30] Foreign Application Priority Data

Jun. 18, 1985 [FR] France ............................... 85 09206

[51] Int. Cl.$^4$ ............................................. C07C 69/52
[52] U.S. Cl. .................................................. 560/223
[58] Field of Search .................................... 560/223

[56] References Cited

U.S. PATENT DOCUMENTS

| | | | |
|---|---|---|---|
| 3,177,187 | 4/1965 | Hollander et al. | 560/223 |
| 3,282,905 | 11/1966 | Fasick et al. | 560/223 |
| 3,283,012 | 11/1966 | Day | 560/223 |
| 3,378,609 | 4/1968 | Fasick et al. | 560/223 |

FOREIGN PATENT DOCUMENTS 42-12883 7/1967 Japan .
9181239 10/1984 Japan .

*Primary Examiner*—Paul J. Killos
*Attorney, Agent, or Firm*—Millen, White & Zelano

[57] ABSTRACT

A process for the preparation of fluoroalkyl (alk)acrylates, having the formula:

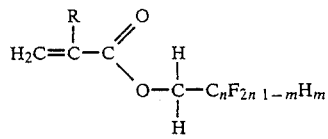

where
$R_1$ is a hydrogen atom, or an alkyl group having up to 4 carbon atoms,
n is between 1 and 20, and
m is between 0 and n, in which an (alk)acrylic anhydride, of the formula:

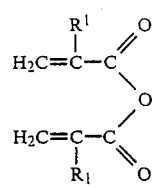

is reacted with a fluoroalcohol of the formula:

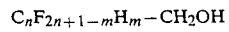

in the presence of at least one acid catalyst, at a temperature between 10° C. and 90° C. and during 3 to 120 minutes.

20 Claims, No Drawings

PROCESS FOR THE PRODUCTION OF FLUOROALKYL ACRYLATES

CROSS-REFERENCE TO RELATED APPLICATIONS

This application is a continuation-in-part of application Ser. No. 875,826 filed June 18, 1986, the contents thereof being incorporated by reference herein.

BACKGROUND OF THE INVENTION

The present invention relates to a new process for the manufacture of fluoroalkyl (alk)acrylates.

Fluoroalkyl (alk)acrylates define compounds of formula:

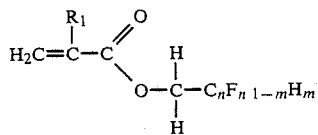

where
- $R_1$ is a hydrogen atom, or an alkyl group having up to 4 carbon atoms, e.g., methyl, ethyl, propyl or butyl
- n is between 1 and 20 and
- m is between 0 and n.

The most common of these compounds are fluoroalkyl methacrylate and acrylate. Where $R_1$ is other than H, the compounds can be named as α-alkyl propenoic fluoroalkyl ester.

Several synthetic routes to these compounds are well known at present.

The first is an esterification reaction between an (alk)acrylic acid and a fluoroalcohol.

It is described particularly in the Japanese patent application 054,511 to 30.3.83, for the synthesis of 2,2,2-trifluoroethyl methacrylate, according to which methacrylic acid and 2,2,2-trifluoroethanol are reacted in the presence of a large excess of sulfuric acid. This reaction takes a very long time. The authors of this patent disclose 75 hours' reaction at 75° C., for a yield which is only 73%.

A second synthetic route consists in reacting a (meth)acryloyl chloride with a fluoroalcohol. For example, U.S. Pat. No. 3,177,187 describes the process for preparing SYM-tetrafluorodichloroisopropyl acrylate and SYM-tetrafluorodichloroisopropyl methacrylate by reacting SYM-tetrafluorodichloroisopropyl alcohol with an acrylic or methacrylic chloride, optionally with an esterification catalyst which is preferably pyridine. The amount of catalyst may range from about 1.0 to 200%, preferably 5 to 50% by weight based on the amount of SYM-tetrafluorodichloroisopropyl alcohol charged. This preparation is effected at reflux temperature for a period of 5.5 hours to 10 hours. The yield of this reaction reaches only 67–75%. Moreover, the operating conditions for this reaction are complex. In fact, the hydrochloric acid produced during the reaction must be prevented from undergoing addition to the double bond, especially that of the (meth)acrylate. This is why the reaction must be carried out in the presence of an organic substance which reacts with hydrochloric acid, for example pyridine, to form a salt which must then be removed from the reaction mixture. Another disadvantage of this reaction lies in the ease with which acryloyl chlorides are hydrolyzed in the presence of moisture.

SUMMARY OF THE INVENTION

The object of the present invention is a new process for the synthesis of fluoroalkyl (alk)acrylates which does not involve the disadvantages of the known processes and which makes it possible to obtain high yields.

Upon further study of the specification and appended claims, further objects and advantages of this invention will become apparent to those skilled in the art.

More precisely, the present invention relates to a new process for the manufacture of fluoroalkyl (alk)acrylates, in which an (alk)acrylic anhydride, of the formula:

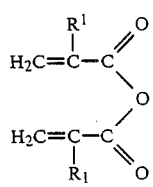

where $R_1$ is a hydrogen atom or an alkyl group having up to 4 carbon atoms, is reacted with a fluoroalcohol which is chosen from those of formula:

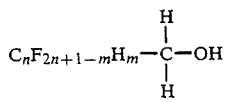

where:
- n is between 1 and 20, and
- m is between 0 and n, in the presence of at least one acid catalyst, at a temperature between 10° C. and 30° C. and during 3 to 120 minutes.

The fluoroalkyl (alk)acrylates obtained are then separated off. According to a preferred embodiment of the invention, the separation is carried out by distillation. The distillation may be performed under reduced pressure and by refraction. However, when the boiling point of the fluoroalkyl (alk)acrylates and that of the (alk)acrylic acid formed in the process according to the invention lie close together, namely with a difference of the order of 10° C. or less, then the separation of the fluoroalkyl (alk)acrylate is advantageously performed in the following manner: water is added to the reaction mixture obtained after the reaction and the (alk)acrylic acid is extracted in the aqueous phase. If appropriate, the remaining traces of (alk)acrylic acid may be removed by neutralization using, for example, sodium hydroxide, followed by separation of the organic phase using liquid/liquid phase separation. The organic phase is then distilled in order to produce a pure fluoroalkyl (alk)acrylates phase.

The process according to the invention is generally performed at atmospheric pressure but it may be also performed under reduced pressure or under high pressure about 10 bars or less.

Preferably, the process according to the invention is performed in the presence of at least one polymerization inhibitor, which is preferably used in an efficient amount.

Preferably, the duration of the reaction according to the invention is between 10 and 30 minutes.

Preferably, the molar ratio of the (alk)acrylic anhydride to the fluoroalcohol is between 1 and 1.2.

During the entire duration of the reaction according to the invention, the temperature of the reaction mixture is preferably maintained between 20° C. and the boiling point of the fluoroalcohol when this point is lower or equal to 90° C. Preferably, the reaction temperature is between 20° and 65° C. Because of the exothermicity of the reaction according to the invention, the procedure is preferably as follows:

In a first stage, the fluoroalcohol one or more polymerization inhibitors and one or more acid catalysts are introduced, and then, after stirring, the (alk)acrylic anhydride is introduced gradually.

The (alk)acrylic anhydrides to which the process according to the invention relates are especially acrylic anhydride and methacrylic anhydride.

Among the fluoroalcohols to which the present invention relates there may be mentioned, in particular, 2,2,2-trifluoroethanol, 2,2,3,3-tetrafluoro-1-propanol and 2,2,3,4,4,4-hexafluoro-1-butanol.

Among the acid catalysts which may be used in the process according to the invention there may be mentioned, in particular, sulfuric acid, para-toluenesulfonic acid, phosphoric acid, hydrochloric acid, cationic resins or Lewis acids such as, for example, zinc chloride, or Fe(III) chloride. These acid catalysts are introduced into the reaction mixture in a molar ratio, relative to the (alk)acrylic anhydride, greater than or equal to $10^{-4}$, and preferably between $10^{-3}$ and $10^{-2}$. The polymerization inhibitor employed may be, in particular, phenothiazine, tert-butyl catechol, hydroquinone methyl ether, hydroquinone, methylene blue, copper sulfate or iron sulfate, in a molar ratio, relative to the (alk)acrylic anhydride, greater than or equal to $10^{-4}$.

The process according to the invention is advantageous in more than one way.

The process according to the invention is very simple, and this facilitates its profitable use at an industrial site.

The yields obtained with the aid of the process according to the invention are high, and in most cases higher than 90%.

The examples given below by way of indication will enable the invention to be understood better.

Without further elaboration, it is believed that one skilled in the art can, using the preceding description, utilize the present invention to its fullest extent. The following preferred specific embodiments are, therefore, to be construed as merely illustrative, and not limitative, of the remainder of the disclosure in any way whatsoever.

In the preceding text and the following examples, all temperatures are set forth uncorrected in degrees Celsius and all parts and percentages are by weight, unless otherwise indicated.

EXAMPLE 1

Preparation of 2,2,2-trifluoroethyl methacrylate

The following charge is introduced into a reactor equipped with a mechanical stirring system and supporting a condenser:

600 g of 2,2,2-trifluoroethanol,
0.808 g of phenothiazine, and
1.19 g of sulfuric acid (100%).

After this charge has been homogenized at ambient temperature, 1,016.4 g of methacrylic anhydride are added continuously and at atmospheric pressure.

During the entire reaction period the temperature of the reaction mixture is maintained at approximately 65° C. under atmospheric pressure.

After half an hour the reaction is completed.

The reaction mixture is then distilled under vacuum.

2,2,2-Trifluoroethanol is distilled as a forerun which comes over between 59° and 74° C. at a pressure of 0.33 bar, and then 2,2,2-trifluoroethyl methacrylate, which distills at 40° C. at 0.066 bar, is recovered. 944.44 g of 2,2,2-trifluoroethyl methacrylate are collected. The yield is 97.6%.

The distillation is finished at 55° C. at 0.02 bar in order to remove the methacrylic acid formed during the reaction.

The 2,2,2-trifluoroethyl methacrylate collected has the following properties:
density at 20° C.: 1.418
vapor pressure at 20° C.: 0.026 bar
boiling point at 1.013 bar: 100° C.

EXAMPLE II

Preparation of 2,2,2-trifluoroethyl methacrylate

The operating procedure followed in this example is in all aspects identical to that described in Example 1, except for sulfuric acid which is added in a quantity of only 0.6 g.

After distillation, 950.36 g of 2,2,2-trifluoroethyl methacrylate are collected. The yield is 94.3%.

EXAMPLE III

Preparation of 2,2,2-trifluoroethyl methacrylate

The following charge is introduced into a reactor fitted with a mechanical stirring system and supporting a condenser:

1,500 g of 2,2,2-trifluoroethanol,
1.92 g of methylene blue,
2,405 g of methacrylic anhydride, 98.5% by weight, and
2.9 g of sulfuric acid (100%).

By then following the operating procedure defined in Example 1, 2,388.6 g of 2,2,2-trifluoroethyl methacrylate are collected after distillation. The yield is 94.7%.

EXAMPLE IV

Preparation of 2,2,2-trifluoroethyl acrylate

The following charge is introduced into a reactor fitted with a mechanical stirring system and supporting a condenser:

200 g of 2,2,2-trifluoroethanol,
0.47 g of copper sulfate,
0.38 g of sulfuric acid (100%), and
315 g of acrylic anhydride.

During the entire period of reaction between the 2,2,2-trifluoroethanol and acrylic anhydride, the temperature of the reaction mixture is maintained below 65° C. under atmospheric pressure.

After 10 minutes the reaction is completed.

The reaction mixture is then distilled under vacuum.

2,2,2-Trifluoroethanol which comes over at 40° C. at 0.33 bar is first distilled off and then 2,2,2-trifluoroethyl ethyl acrylate, which distills at 63° C. at 0.33 bar, is recovered. 295 g of 2,2,2-trifluoroethyl acrylate are collected in this manner. The yield is 95.7%.

EXAMPLE V

Preparation of 2,2,3,4,4,4-hexafluorobutyl methacrylate

The following charge is introduced into a reactor fitted with a mechanical stirring system and supporting a condenser:

1,820 g of 2,2,3,4,4,4-hexafluoro-1-butanol,
1,694 g of methacrylic anhydride,
3.00 g of sulfuric acid (100%), and
2.35 g of iron sulfate.

The temperature is maintained at 65° C. during the reaction under atmospheric pressure. After half an hour the reaction is completed. Separation of the 2,2,3,4,4,4-hexafluorobutyl methacrylate formed is carried out next.

3,500 ml of distilled water are then added to the reaction mixture and, after stirring, the aqueous phase is separated from the organic phase by liquid/liqiid phase separation.

After distillation of the organic phase at 0.066 bar and at 78° C., 2,420 g of 2,2,3,4,4,4-hexafluorobutyl methacrylate are obtained, with the following properties:
density at 25° C.: 1.338
refractive index at 25° C.: 1.3512.
The reaction yield is 96.8%.

EXAMPLE VI

Preparation of 2,2,3,4,4,4-hexafluorobutyl acrylate

The following charge is introduced into a reactor fitted with a mechanical stirring system and supporting a condenser:

910 g of 2,2,3,4,4,4-hexafluoro-1-butanol,
1.4 g of sulfuric acid (100%),
1.2 g of copper sulfate, and then
661.5 g of acrylic anhydride.

The temperature is maintained at 65° C. during the reaction under atmospheric pressure. After a quarter of an hour the reaction is completed.

The isolation of 2,2,3,4,4,4-hexafluorobutyl acrylate is performed as indicated in Example V.

After distillation at 0.066 bar at 70° C., 1,147 g of 2,2,3,4,4,4-hexafluorobutyl acrylate are collected, with the following properties:
density at 25° C.: 1.389
refractive index at 25° C.: 1.3492.
The reaction yield is 97.2%.

EXAMPLE VII

Preparation of 2,2,3,3-tetrafluoropropyl methacrylate

The following charge is introduced into a reactor fitted with a mechanical stirring system and supporting a condenser:

1,340 g of 2,2,3,3-tetrafluoro-1-propanol,
2.9 g of sulfuric acid (100%),
1.6 g of phenothiazine, and then
1,617 g of methacrylic anhydride.

The temperature is maintained at 65° C. during the reaction under atmospheric pressure. After half an hour the reaction has ended. Separation of the 2,2,3,3-tetrafluoropropyl methacrylate formed is then performed. 2,000 ml of distilled water are added to the reaction mixture and, after stirring, the aqueous phase is separated from the organic phase by liquid/liquid phase separation.

After distillation of the organic phase at 0.066 bar and at 73° C., 1,959.5 of 2,2,3,3-tetrafluoropropyl methacrylate are collected, with the following properties:
density at 25° C.: 1.255
refractive index at 25° C.: 1.3723.
The reaction yield is 97%.

EXAMPLE VIII

Preparation of 2,2,3,3-tetrafluoropropyl acrylate

The following charge is introduced into a reactor fitted with a mechanical stirring system and supporting a condenser:

1,340 g of 2,2,3,3-tetrafluoro-1-propanol,
2.8 g of sulfuric acid (100%),
1.6 g of phenothiazine, and then
1,384 g of acrylic anhydride.

The temperature is maintained at 65° C. during the reaction under atmospheric pressure. After half an hour the reaction has ended. The isolation of 2,2,3,3-tetrafluoropropyl acrylate is then performed as indicated in Example VII.

After distillation at 0.066 bar and at 63° C., 1,844 g of 2,2,3,3-tetrafluoropropyl acrylate are collected, with the following properties:
density at 25° C.: 1.308
refractive index at 25° C.: 1.3628.
The reaction yield is 98.1%.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of fluoroalkyl (alk)acrylates, having the formula $$\begin{array}{c} R_1 \quad\quad O \\ | \quad\quad\quad \| \\ H_2C=C-C \\ \quad\quad\quad \backslash \quad H \\ \quad\quad\quad\quad\quad | \\ \quad\quad\quad\quad O-C-C_nF_{2n+1-m}H_m \\ \quad\quad\quad\quad\quad | \\ \quad\quad\quad\quad\quad H \end{array}$$

where
$R_1$ is a hydrogen atom, or an alkyl group having up to 4 carbon atoms,
n is between 1 and 20, and
m is between 0 and n, in which an (alk) acrylic anhydride, of the formula $$\begin{array}{c} R^1 \quad\quad O \\ | \quad\quad\quad \| \\ H_2C=C-C \\ \quad\quad\quad \backslash \\ \quad\quad\quad\quad O \\ \quad\quad\quad / \\ H_2C=C-C \\ | \quad\quad\quad \backslash\!\!\! \| \\ R_1 \quad\quad O \end{array}$$

is reacted with a fluoroalcohol of the formula:

$$C_nF_{2n+1-m}H_m-CH_2OH$$

in the presence of at least one acid catalyst, at a temperature between 10° C. and 90° C. and during 3 to 120 minutes to obtain fluoroalkyl (alk)acrylates in a yield of at least 90%.

2. The process as claimed in claim 1, wherein, during the entire period of reaction between the (alk)acrylic anhydride and the fluoroalcohol the temperature of the reaction mixture is maintained between 20° C. and the boiling point of the fluoroalcohol.

3. The process as claimed in claim 1, wherein during the entire period of reaction between the (alk)acrylic anhydride and the fluoroalcohol the temperature of the reaction mixture is maintained between 20° C. and 65° C.

4. The process as claimed in claim 1, wherein the fluoroalcohol, at least one polymerization inhibitor and at least one acid catalyst are introduced first of all, and then the (alk)acrylic anhydride is introduced gradually.

5. The process as claimed in claim 1, wherein the molar ratio of the (alk)acrylic anhydride to the fluoroalcohol is between 1 and 1.2.

6. The process as claimed in claim 1, wherein the duration of the reaction is between 10 and 30 minutes.

7. The process as claimed in claim 1, wherein the fluoroalcohol is 2,2,2-trifluoroethanol.

8. The process as claimed in claim 1, wherein the quantity of acid catalyst introduced is such that the molar ratio of this catalyst to the (alk)acrylic anhydride is greater than or equal to $10^{-4}$.

9. The process as claimed in claim 1, wherein the reaction is performed in the presence of an inhibiting amount of polymerization inhibitor.

10. The process as claimed in claim 9, wherein the quantity of polymerization inhibitor introduced is such that the molar ratio of this inhibitor to (alk)acrylic anhydride is greater than or equal to $10^{-3}$.

11. The process as claimed in claim 1, wherein the fluoroalkyl (alk)acrylate obtained is separated off by distillation.

12. The process as claimed in claim 9, wherein the polymerization inhibitor is selected from phenothiazine, tert-butyl catechol, hydroquinone methyl ether, hydroquinone, methylene blue, copper sulfate or iron sulfate.

13. The process as claimed in claim 4, wherein the (alk)acrylic anhydride is acrylic anhydride or methacrylic anhydride.

14. The process as claimed in claim 1, wherein the acid catalyst is selected from sulfuric acid, para-toluene sulfonic acid, phosphoric acid, hydrochloric acid, cationic resins or a Lewis acid.

15. The process as claimed in claim 14, wherein the catalyst is zinc chloride or Fe III chloride.

16. The process as claimed in claim 4, wherein the molar ratio of the (alk)acrylic anhydride to the fluoroalcohol is between 1 and 1.2.

17. The process as claimed in claim 16, wherein the duration of the reaction is between 10 and 30 minutes.

18. The process as claimed in claim 17, wherein the fluoroalcohol is 2,2,2-trifluoroethanol.

19. The process as claimed in claim 18, wherein the quantity of acid catalyst introduced is such that the molar ratio of this catalyst to the (alk)acrylic anhydride is greater than or equal to $10^{-4}$.

20. The process as claimed in claim 19, wherein the reaction is performed in the presence of an inhibiting amount of polymerization inhibitor.

* * * * *